(12) United States Patent
Li et al.

(10) Patent No.: US 11,840,698 B2
(45) Date of Patent: Dec. 12, 2023

(54) **RICE *PAL1* GENE, AND ENCODING PROTEIN AND USE THEREOF**

(71) Applicant: Institute of Crop Sciences, Chinese Academy of Agricultural Sciences, Beijing (CN)

(72) Inventors: Xueyong Li, Beijing (CN); Yan Chun, Beijing (CN); Jinfeng Zhao, Beijing (CN); Jingjing Fang, Beijing (CN); Shoujiang Yuan, Beijing (CN)

(73) Assignee: Institute of Crop Sciences, Chinese Academy of Agricultural Sciences, Beijing (CN)

( * ) Notice: Subject to any disclaimer, the term of this patent is extended or adjusted under 35 U.S.C. 154(b) by 0 days.

(21) Appl. No.: 17/488,544

(22) Filed: Sep. 29, 2021

(65) Prior Publication Data

US 2022/0119833 A1    Apr. 21, 2022

(30) Foreign Application Priority Data

Oct. 19, 2020  (CN) .......................... 202011115105.3

(51) Int. Cl.
*C12N 15/82*    (2006.01)

(52) U.S. Cl.
CPC ................ *C12N 15/8223* (2013.01)

(58) Field of Classification Search
None
See application file for complete search history.

(56) References Cited

U.S. PATENT DOCUMENTS 8,299,321 B2 * 10/2012 Cao ...................... C07H 21/04
536/23.6
2012/0227131 A1 * 9/2012 Abad ................. C12N 15/8247
800/320.2

OTHER PUBLICATIONS

Luo et al., Planta 221:222-230, 2005 (Year: 2005).*
Sequence Accession AC091532, Jun. 22, 2007, sequence alignment attached to office action (Year: 2007).*

* cited by examiner

*Primary Examiner* — Brent T Page
(74) *Attorney, Agent, or Firm* — Clark & Elbing LLP

(57) ABSTRACT

The present disclosure relates to a rice PAL1 gene, an encoding protein and use thereof. The rice PAL1 gene has the nucleotide sequence shown in SEQ ID NO. 1, and the rice PAL1 protein has the amino acid sequence shown in SEQ ID NO. 4. Mutation of the gene leads to reduction of rice plant height and panicle length, while decreasing the number of primary branches, secondary branches and grains per panicle. It is found that the PAL1 gene can restore a mutant panicle type to a normal phenotype. The present disclosure provides a PAL1 gene functioning as a regulator of the rice panicle length and an encoding protein thereof. A rice panicle type is an important trait influencing rice yield. Therefore, it will be desired to directionally design a plant type and improve the rice yield by regulating panicle traits of rice with the PAL1 gene.

1 Claim, 8 Drawing Sheets

Specification includes a Sequence Listing.

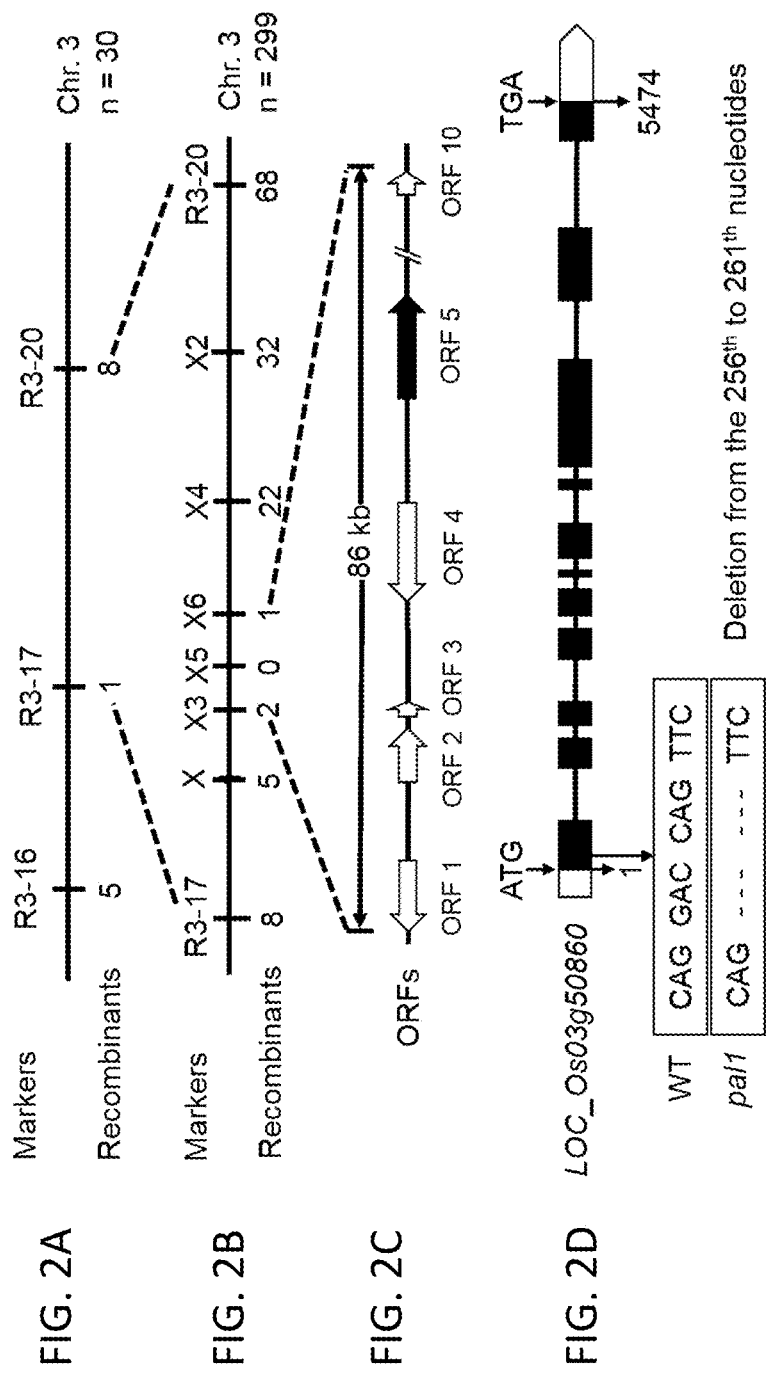

WT  pal1  B590-1  B590-2

WT  pal1  B590-1  B590-2

R: Root   S: Stem   LB: Leaf blade
LS: Leaf sheath   SB: Shoot base

RICE *PAL1* GENE, AND ENCODING PROTEIN AND USE THEREOF

SEQUENCE LISTING

This application contains a Sequence Listing which has been filed electronically in ASCII format and is hereby incorporated by reference in its entirety. Said ASCII copy, created on Sep. 28, 2021, is named 51616-002001_Sequence_Listing_9_28_21_ST25.txt and is 39,928 bytes in size.

TECHNICAL FIELD

The present disclosure relates to the field of gene engineering, and in particular to a rice PAL1 gene, and an encoding protein and use thereof.

BACKGROUND ART

Rice (*Oryza sativa* L.) is one of the important food crops in China, and its yield and quality directly affect food security and people's living standards in China. Rice panicle type has always been one of the important contents of rice genetics and breeding research, and it is an important trait that affects rice yield. The structure of the rice panicle consists of a main axis, primary branches, secondary branches, and spikelets growing on the branches. According to the length of the rachis, the number of branches, the number of spikelets, and the presence of erect trait, the rice panicle types can be divided into long and short panicles, sparse and dense panicles, and drooping and erect panicles.

In recent years, with the completion of whole genome sequencing of rice and the development of rice molecular biology and functional genomics of rice, a plurality of genes related to panicle development have been mapped and cloned by means of genetic populations and mutants. Although these genes have different effects, they are basically involved in the formation of rachis branch meristems, and the regulation of the size of rachis branch meristems, the transition time from branch meristems to spikelet meristems, and the elongation of branches.

LAX1 gene encodes a bHLH transcription factor, which is involved in the initiation and maintenance of the axillary meristem on the main axis of rice panicle, forming the lateral meristem of rice inflorescence. In a lax1 mutant with a mild phenotype, the number of branches and the number of grains per panicle decrease. A lax1 mutant with a severe phenotype has only rachises, without branches and seed setting. LAX2 can interact with LAX1 and is a nucleoprotein including plant-specific conserved domains. The lax2 single mutant has a sparse panicle type, and the lax1 and lax2 double mutant has an enhanced sparse panicle phenotype. RCN1 and RCN2 play an important role in determining the morphology of rice panicles by controlling the phase transition time. Their constitutive expression delays the transition from vegetative growth to reproductive growth, leading to a sharp increase in the number of branches and tighter panicle morphology. The dominant allelic variation of DEP1 gene can promote cell division, reduce the length of the panicle neck node, make the panicle denser, and increase the number of branches and the number of grains per panicle. IPA1, which encodes a transcription factor OsSPL14, can promote the formation of rice panicle branches through positive regulation of DEP1. In vegetative growth and reproductive growth phases, IPA1 is highly expressed in apical meristems and primary and secondary branches. FZP functions as an ERF transcriptional activator and promotes the development of rice spikelets. The branches of fzp mutant is normally developed, but spikelets cannot be differentiated on the rachis branch, and next order branches are continuously produced where the spikelets originally are formed. SPI, a gene involved in the regulation of rice panicle length, is highly expressed in the phloem of young panicles and encodes a polypeptide transporter protein. Scanning electron microscopy shows that the mutant is not different from the wild type in the vegetative growth phase and early developmental phase, but defects occurred during the elongation of the rice panicle branches, which result in the delayed or degraded primary rachis branch development during the development of the rice panicle, thereby reducing the number of primary branches. Gn1a is a major QTL that affects the filled number of grains per panicle of rice, and encodes a cytokinin oxidase/dehydrogenase OsCKX2 that degrades cytokinins. The downregulation of Gn1a expression leads to the accumulation of cytokinin in the inflorescence meristem, increases the spikelet number per panicle, further increases the number of grains per panicle, and ultimately increases rice yield.

Over the past few decades, great progress has been made in the research on relevant factors and regulatory pathways that control the phenotype of rice inflorescences, such as auxin signals and cytokinin signals that specifically act on rice inflorescence development. However, although some genes related to rice panicle development have been identified at present, specific action mode thereof remain unknown, and the number of reported genes with panicle development regulation functions is not abundant enough. Therefore, further excavation and in-depth study of rice panicle type regulating genes are of great significance to clarify the genetic mechanism of rice panicle development, and also provide a sufficient theoretical basis for high-yield rice breeding.

SUMMARY

An objective of the present disclosure is to provide a rice PAL1 gene capable of regulating rice panicle type, an encoding protein and use thereof.

To achieve the objective of the present disclosure, the technical solutions of the present disclosure are as follows:

The present disclosure provides a rice PAL1 protein, being any one of the following protein shown in 1) or 2):

1) having the amino acid sequence shown in SEQ ID NO. 4; and 2) a protein having the amino acid sequence shown in SEQ ID NO. 4 with the substitution, deletion, or insertion of one or more amino acids, but having the same function as the PAL1 protein shown in SEQ ID NO. 4.

Furthermore, the present disclosure provides a gene encoding the foregoing protein.

Specifically, the gene has any one of the following nucleotide sequences shown in 1) to 3):

1) the nucleotide sequence shown in SEQ ID NO. 1;

2) a sequence formed by the substitution, deletion, or insertion of one or more nucleotides in the nucleotide sequence shown in SEQ ID NO. 1; and 3) the nucleotide sequence capable of hybridizing with the nucleotide sequence in 1) or 2) and encoding the same functional protein under stringent conditions.

Furthermore, the present disclosure provides a vector including the gene, and a host cell including the gene or the vector. The vector may include a plant expression vector pCAMBIA1305.1 or a derived vector thereof; the host cell may include *Agrobacterium* cells and *Escherichia coli* cells.

The vector and the host cell may be understood as those used by those skilled in the art in the transgenic process, and the host cell may not have the ability to develop into an individual plant. However, with the development of science and technology, there may be changes in the selection of the vector and host cell, or in the application field for non-transgenic purpose, use of the vector and the host cell may be involved. However, any one including the gene of the present disclosure or the vector of the present disclosure should be within the protection scope of the present disclosure.

In addition, the present disclosure provides a use of the gene in regulating rice plant height and panicle type. The use includes a use of the PAL1 protein or encoding gene of the present disclosure in improving the rice plant height or panicle type.

In the present disclosure, it is found through experiments that the plant height of a rice pal1 mutant with PAL1 gene mutation is 15.2% lower than that of a wild-type plant.

From the analysis of the panicle type, panicle length of the pal1 mutant is reduced, and number of primary and secondary branches, and number of grains per panicle are significantly reduced. Herein, the panicle length is reduced by 25.6% compared with the wild type, and the number of primary and secondary branches, and the number of grains per panicle are reduced by 22.0%, 45.9%, and 40.2%, respectively, compared with the wild type.

In view of this, the present disclosure further provides a use of the PAL1 gene in preparing transgenic plants.

The preparation of transgenic plants is a conventional technical means in the art, and the present disclosure does not make additional limitations. The technical solutions for transgenic rice breeding using the genes of the present disclosure are all within the protection scope of the present disclosure.

Therefore, the present disclosure provides a use of a rice PAL1 protein, an encoding gene of the rice PAL1 protein, or a biomaterial including the encoding gene of the rice PAL1 protein in regulating rice panicle length, number of branches, or number of grains per panicle.

The present disclosure provides a use of a rice PAL1 protein, an encoding gene of the rice PAL1 protein, or a biomaterial including the encoding gene of the rice PAL1 protein in increasing rice panicle length, number of branches, or number of grains per panicle.

The present disclosure provides a use of a rice PAL1 protein, an encoding gene of the rice PAL1 protein, or a biomaterial including the encoding gene of the rice PAL1 protein in improving of germplasm resources of rice panicle types.

The present disclosure provides a use of a rice PAL1 protein, an encoding gene of the rice PAL1 protein, or a biomaterial including the encoding gene of the rice PAL1 protein in preparing transgenic rice with high number of grains per panicle or high yield.

In the present disclosure, it is further found through experiments that transforming the PAL1 gene of the present disclosure into a rice pal1 mutant may restore the mutant to a normal panicle phenotype. Therefore, the PAL1 gene of the present disclosure may directly regulate the size of the rice panicle type.

The present disclosure provides a mutant gene of a rice PAL1 gene, wherein the mutant gene has 6 bases deleted at positions 256 to 261 from the initiation codon of the rice PAL1 gene, and a deleted sequence is "gaccag". That is, the sequence of the mutant gene of the rice PAL1 gene is a sequence deleted from positions 256 to 261 of a CDS sequence of the rice PAL1 gene shown in SEQ ID NO. 3.

The present disclosure provides a use of the mutant gene of a rice PAL1 gene or a biomaterial including the gene in lowering rice plant height or preparing dwarf transgenic rice.

The present disclosure has the following beneficial effects: The present disclosure firstly provides a PAL1 gene having effects on rice plant height and panicle size and an encoding protein thereof. The present disclosure has verified that the gene has the function of regulating the rice plant height and panicle type through experiments. PAL1 gene mutation leads to significant decreases in plant height and panicle length, while supplementing the gene can significantly increase the plant height and panicle size of the mutant. The technical solutions provided by the present disclosure provide a new direction for the breeding of rice and the preparation of transgenic rice, and the construction of transgenic rice transformed with the gene can be beneficial to the increase of rice yield.

BRIEF DESCRIPTION OF THE DRAWINGS

FIGS. 1A-1I illustrate phenotypes of wild-type Huaidao No. 5 and pal1 mutant provided by the present disclosure, in which FIG. 1A illustrates the plant phenotype, FIG. 1B illustrates closed panicle types, FIG. 1C illustrates patulous panicle types, and FIG. 1D illustrates patulous branches, FIG. 1E to 1I illustrate the statistical analysis of plant height, panicle length, number of primary branches, number of secondary branches, and number of grains per panicle.

FIGS. 2A-2D illustrate the mapping and structure of the PAL1 gene of the present disclosure.

FIG. 4A illustrates closed panicle types, and FIG. 4B illustrates patulous panicle types. FIGS. 4C to 4F illustrate the statistical analysis of panicle length, number of primary branches, number of secondary branches, and number of grains per panicle. In $T_0$ transgenic plants, a total of 15 independent transformed lines are obtained, 10 of which are restored to wild-type phenotypes, named B590-1, B590-2, . . . B590-10, respectively; investigation and statistics are made on panicle traits of transgenic plants B590-1 and B590-2, and results show that the panicle length, the number of primary branches, the number of secondary branches, and the number of grains per panicle are significantly greater in the transgenic plants than in the pal1 mutant, and reach the wild-type levels. All of the other 8 transgenic plants, B590-3 to B590-10, have similar phenotypes.

FIG. 6C illustrates a statistical analysis of the longitudinal section area of the apical meristem; FIG. 6D and FIG. 6E illustrate scanning electron microscopic observations of the apical meristem and young panicle primordia; FIG. 6F and FIG. 6G illustrate statistical analyses of the longitudinal area of the apical meristem and the number of primary rachis branch primordia, respectively.

DETAILED DESCRIPTION OF THE EMBODIMENTS

Figure 1A:
Figure 1B:
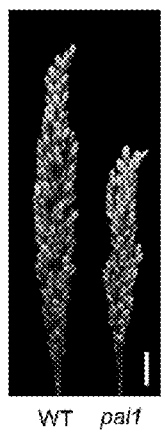
Figure 1C:
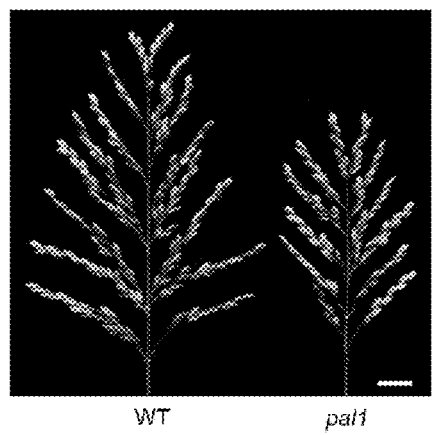
Figure 1D:
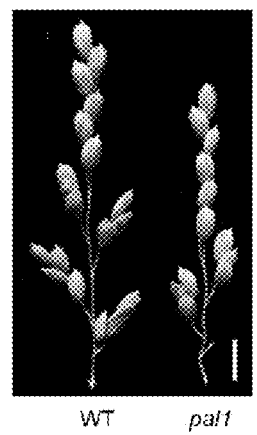
Figure 1E:
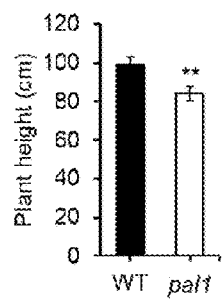
Figure 1F:
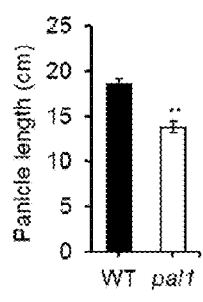
Figure 1G:
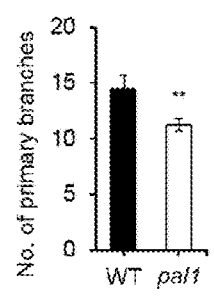
Figure 1H:
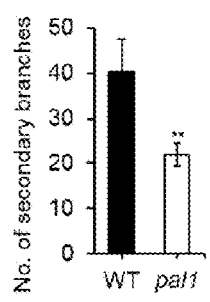
Figure 1I:
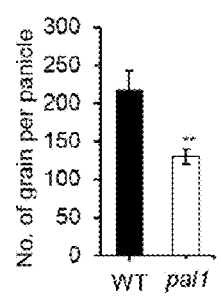

The preferred implementation of the present disclosure will be described in detail below in conjunction with examples.

All experimental methods used in the following examples are conventional methods, unless otherwise specified. All materials and reagents used in the following examples can be commercially available, unless otherwise specified.

Example 1 Acquisition and Phenotypic Analysis of pal1 Mutant

A mutant pal1 (panicle length 1) with lower plant height and shorter panicle length was obtained by radiation mutagenesis of a japonica rice cultivar Huaidao No. 5 by $^{60}$Co-γ irradiation (Yuan C Y, Yuan S T, Wen Z H, et al. Characteristics and high-yielding cultivation technique of Huaidao No. 5[J]. China Rice, 2002, (4): 14). Twenty samples of wild type and pal1 mutants were selected, respectively; statistical analyses were conducted on their plant height, panicle length, number of primary branches, number of secondary branches, and number of grains per panicle. The analysis results showed that the plant height of the rice pal1 mutant was significantly lowered by 15.2% compared with the wild type (A and E in FIG. 1). Compared with the wild type, the panicle length of the pal1 mutant was significantly shortened by 25.6%, and the number of primary branches and the number of secondary branches were also significantly reduced by 22.0% and 45.9%, respectively (B, C, D, F, G and H in FIG. 1); eventually, the number of grains per panicle was significantly reduced by 40.2% (I in FIG. 1).

Example 2 Acquisition of Rice PAL1 Gene

The pal1 mutant was crossed with the indica rice cultivar Dular with normal phenotype and high nucleotide acid polymorphism to obtain $F_1$, $F_1$ was selfed to obtain $F_2$ segregation population, and the $F_2$ population was used for genetic analysis and gene mapping. The analysis of the lines with trait segregation in the $F_2$ showed that the normal plant and the mutant plant met a segregation ratio of 3:1, which indicated that the mutant trait was controlled by a pair of recessive genes.

With 30 $F_2$ mutants as materials, primary mapping was conducted by using a plurality of InDel markers developed by the alignment of the whole genome sequence of the indica rice cultivar Dular sequenced in this experiment to the genome sequence of a japonica rice cultivar Nipponbare provided on NCBI (National Center for Biotechnology Information) and uniformly distributed on 12 chromosomes of rice; candidate genes were mapped between R3-17 and R3-20 markers on chromosome 3 (A in FIG. 2). In order to further finely map the candidate genes, the $F_2$ mapping population continued to be expanded to 299 plants, while developing new markers X1, X2, X3, X4, X5, and X6 for linkage analysis (see Table 1 for the primers used); it was found that recombination events occurred at these markers were 5, 32, 2, 22, 0, and 1, respectively, indicating that the candidate genes were mapped between X3 and X6 (B in FIG. 2).

The physical distance between the two markers X3 and X6 is 86 kb (C in FIG. 2). According to the gene annotation information provided by the Rice Genome Annotation Project (rice.uga.edu/), there are 10 genes between the markers X3 and X6 (C in FIG. 2). Herein, the function of the gene numbered LOC_Os03g50860 is inferred to be related to the phenotype. For this reason, the full-length genomic DNA of this gene is subjected to segmental PCR amplification. Each segment is about 1.5 kb in size, with a total of 6 fragments (see Table 2 for the primers used). DNAStar software is used to analyze the sequencing results of the wild type and mutants. The analysis results show that in the pal1 mutant, a total of 6 bases from positions 256 to 261 after the initiation codon of the gene are deleted (D in FIG. 2), resulting in the deletion of one aspartic acid and one glutamine. The full length of PAL1 genomic DNA is 6249 bp (including 5'UTR and 3'UTR) (as shown in SEQ ID NO. 1), which contains 11 exons; the CDS has a full length of 3018 bp (as shown in SEQ ID NO. 3), encoding a protein consisting of 1013 amino acids (as shown in SEQ ID NO. 4). The primer sequences of the molecular markers involve in Example 2 are shown in Table 1.

TABLE 1

The primer sequences of the molecular markers

| Molecular marker | Sequence of forward primer (5'-3') | SEQ ID NO. | Sequence of reverse primer (5'-3') | SEQ ID NO. |
|---|---|---|---|---|
| R3-16 | AAGGTTAGGCGTGGATTCCTC | 5 | GAGATGAAGGAATGTTCAGTCC | 6 |
| R3-17 | TGGGCTATTATTGGGCTTTG | 7 | CGTGGGATAAAACCACCAAG | 8 |
| R3-20 | CAACTGCCCAGCTATATTGC | 9 | TTTGGGACGGAGGAAGTAGT | 10 |
| X1 | TGCTGCCGGCGATTAACAACT | 11 | TTCGAGACGGGGATTTGATG | 12 |
| X2 | GATGGGTTCGCATCGTCAC | 13 | CTTACCCAGTCTCGAGGTAG | 14 |
| X3 | GACTCAGAGACGGGGACTAG | 15 | CGTGGCGACTGATCAGCG | 16 |
| X4 | TGGAGAGAGTACAGTACTAC | 17 | GAAGCATTGTACTTCTAGTC | 18 |
| X5 | AGGCGCGTAGAATTCCTAGT | 19 | AAAGCTGCCCAAACTATGCG | 20 |
| X6 | GCTTATGCGTCACATCACTAC | 21 | AAAGGTTTGCGTACAGCGAG | 22 |

The sequencing primer sequences involved in Example 2 were shown in Table 2.

TABLE 2

The sequencing primer sequences

| Name of primer | Forward sequence (5'-3') | SEQ ID NO. | Reverse sequence (5'-3') | SEQ ID NO. |
|---|---|---|---|---|
| Frag_1 | AAGTCAACGGTGTCATACGA | 23 | CATGGTCTTGATGATCCACC | 24 |
| Frag_2 | GTGTGGCTGATGAATCTTCT | 25 | GGTGTTCTGATCTCATGAGA | 26 |

TABLE 2-continued

The sequencing primer sequences

| Name of primer | Forward sequence (5'-3') | SEQ ID NO. | Reverse sequence (5'-3') | SEQ ID NO. |
|---|---|---|---|---|
| Frag_3 | CTTGGAGTCGC TACGATAATG | 27 | CTGGACGGTA ATGGGTGCAA | 28 |
| Frag_4 | CAAGCTGACAG CTCAACTTC | 29 | GATAGTCAAC GAGGTGGCAC | 30 |
| Frag_5 | CAAGGTAAACC TCAGAGTGGC | 31 | CCAGCAACAC ACCTGTGGCT | 32 |
| Frag_6 | TTGTTGCTCTT CAACAGAGG | 33 | CATGTTAGCC ACGATGCCTC | 34 |

Example 3 pCAMBIA1305.1::PAL1 Vector Transformed Rice pal1 Mutant

Figure 3:
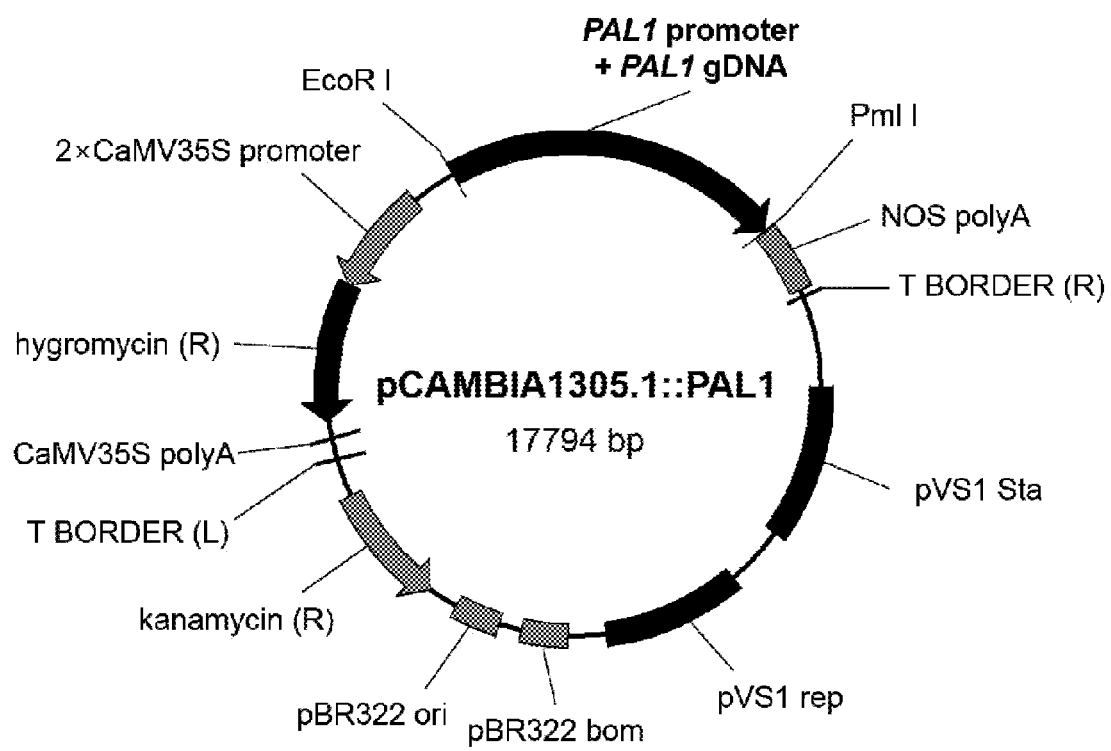
FIG. 3 is a schematic diagram of the structure of the vector pCAMBIA 1305.1::PAL1 of the present disclosure.
Figure 4A:
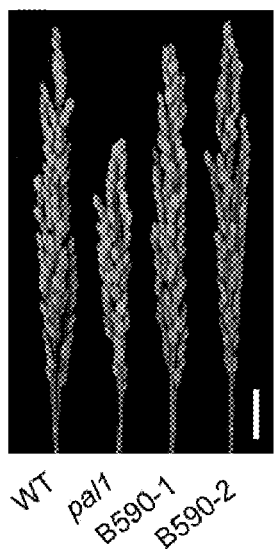
FIGS. 4A-4F illustrate a comparison of panicle types of wild-type, pal1 mutant, and PAL1 transgenic complementary plants. Herein.
Figure 4B:
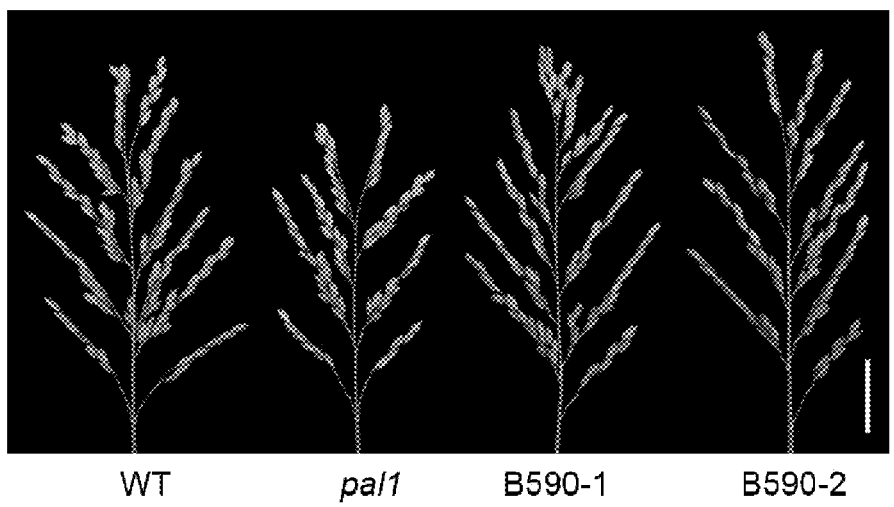
Figure 4C:
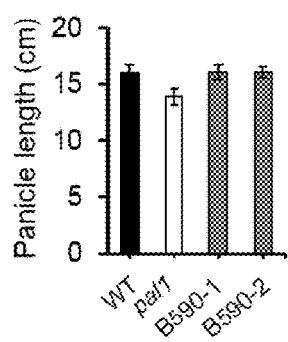
Figure 4D:
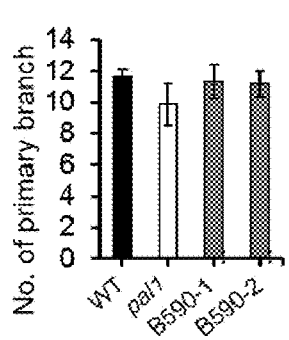
Figure 4E:
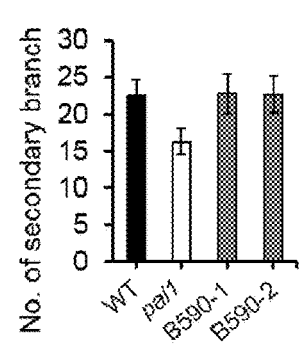
Figure 4F:
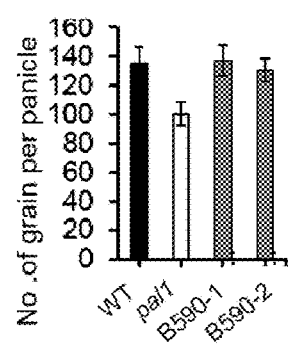

In order to carry out a functional complementation assay, a functional complementary vector driven by the PAL1 gene promoter was constructed. A fragment of 2525 bp upstream of the translation initiation site ATG was selected as the promoter of the gene, and the promoter region and the genomic DNA (without 3'UTR) were amplified simultaneously. One EcoRI site was introduced into the 5'-end of the amplified fragment and one PmlI site was introduced into the 3'-end. The PCR product was 8836 bp in length (including the homologous sequence on the vector). Finally, the PAL1 gene promoter and the entire genome of 8802 bp (shown in SEQ ID NO. 2) were ligated between the EcoRI and PmlI sites of the pCAMBIA1305.1 vector to form a complementary vector driven by its own promoter (FIG. 3).

The constructed complementary vector was transformed into *Agrobacterium* EHA105 and infected the callus induced from the pal1 mutant seeds. In the T₀ transgenic plants, a total of 15 independent transformed lines were obtained, 10 of which were restored to the wild-type phenotypes. Investigation and statistics were made on panicle traits of transgenic plants, and results showed that the panicle length, the number of primary branches, the number of secondary branches, and the number of grains per panicle were significantly greater in the transgenic plant (B590) than in the pal1 mutant, and reached the wild-type levels (A-F in FIG. 4). These results indicated that the reduced panicle type of the pal1 mutant was indeed caused by PAL1 gene mutation. The primer sequences involved in Example 3 were shown in Table 3.

TABLE 3

The sequences of primers for PAL1 gene amplification

| Name of primer | Forward sequence (5'-3') (SEQ ID NO. 35) | Reverse sequence (5'-3') (SEQ ID NO. 36) |
|---|---|---|
| promPAL1 | CCATGATTACGAATTC CGTGAACAATGTCTAC GTAGGAGG | GTCACCAATTCACACG TGCTACCAGCCTACAG CATAGTACTC |

Example 4 Expression Pattern of Rice PAL1 Gene

Figure 5:
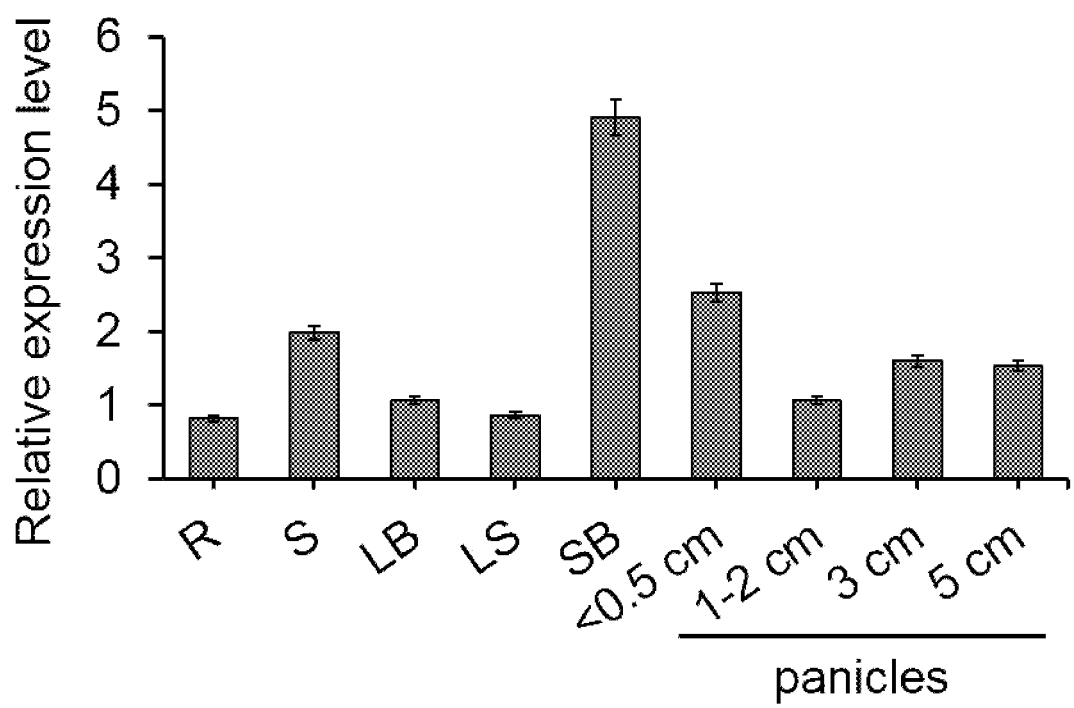
FIG. 5 illustrates an expression pattern analysis of the PLA1 gene of the present disclosure in various tissues of rice.
Figure 6A:
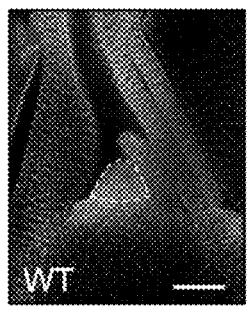
FIGS. 6A-6G illustrate changes in the apical meristem and young panicle primordium of the rice pal1 mutant of the present disclosure. Herein, FIG. 6A and FIG. 6BB are the longitudinal section of the apical meristem.
Figure 6B:
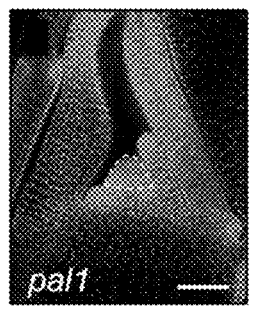
Figure 6D:
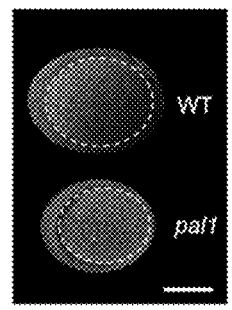
Figure 6E:
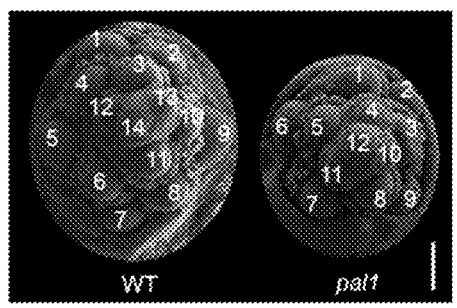
Figure 6C:
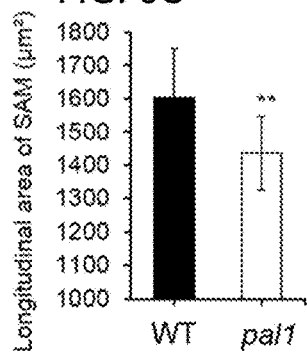
Figure 6F:
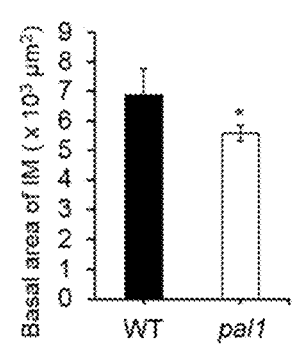
Figure 6G:
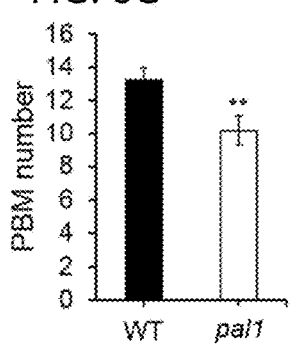

In order to clarify the tissue expression pattern of the PAL1 gene, real-time qPCR was used to detect the expression levels of the gene in various tissues of rice, including root, stem, leaf blade, shoot base, leaf sheath, and young panicles of different lengths. The results showed that the PAL1 gene was expressed in all tissues of rice, with higher expression in the stem and panicles, and the highest expression in the shoot base (FIG. 5). The expression intensity of the PAL1 gene in different organs and parts was consistent with the functional role of the gene. The primer sequences involved in Example 4 were shown in Table 4.

TABLE 4

The sequences of primers used in real-time qPCR

| Name of primer | Forward sequence (5'-3') | SEQ ID NO. | Reverse sequence (5'-3') | SEQ ID NO. |
|---|---|---|---|---|
| Ubiquitin | AACCAGCTGA GGCCCAAGA | 37 | ACGATTGATTTA ACCAGTCCATGA | 38 |
| qPAL1 | CAAGATTCCA ATAGCCCAGC | 39 | GCCTGTCGCTTC ATCGTC | 40 |

Example 5 the Effects of pal1 on Apical Meristem and Panicle Primordia

In order to clarify how the pal1 shortened the panicle length and reduced the yield, the meristem development was observed in the vegetative and reproductive growth phases. In the vegetative growth phase, the longitudinal sections of the shoot apical meristems (SAMs) of the wild type and the pal1 mutant were observed under a laser scanning confocal microscope. The results showed that compared with the wild type, the apical meristem of the pal1 mutant became smaller significantly (A and B in FIG. 6). Statistical analysis showed that the longitudinal section area of the apical meristem of the pal1 mutant was significantly reduced (C in FIG. 6). At the same time, using scanning electron microscopy, observations were conducted on the apical meristems in the critical period of vegetative growth and reproductive growth phases, as well as the formation of primary rachis branch primordia in the reproductive growth phase. The results showed that the apical meristem of the pal1 mutant in the vegetative growth phase was significantly smaller than that of the wild type (D in FIG. 6). At the same time, the number of primary primordia were reduced by 2-4 (E in FIG. 6). Statistical analysis showed that both the longitudinal area of the apical meristem and the number of primary rachis branch primordia of the pal1 mutant were significantly reduced (F and G FIG. 6). Therefore, pal1 may influence the activity of the meristem, making the apical meristem smaller and reducing the number of rachis branch primordial. Ultimately, the panicle length was shortened, the number of branches and the number of grains per panicle were reduced, and the yield was lowered.

Although the general description and specific embodiments have been used to describe the present disclosure in detail above, it is apparent to those skilled in the art that some modifications or improvements can be made on the basis of the present disclosure. Therefore, these modifications or improvements made without departing from the spirit of the present disclosure fall within the protection scope of the present disclosure.

The invention claimed is:

1. A method for increasing yield of rice, wherein the method comprises transforming a PAL1 gene into the rice: wherein the PAL1 gene comprises the nucleotide sequence of SEQ ID NO. 1 and encodes a PAL1 protein; wherein the method comprises using a rice PAL1 protein, an encoding gene of the rice PAL1 protein, or a biomaterial comprising the encoding gene of the rice PAL1 protein; wherein the rice PAL1 protein has the amino acid sequence shown in SEQ ID NO. 4; and wherein the transforming comprises delivering a biomaterial comprising the PAL1 gene to the rice; wherein the encoding gene of the rice PAL1 protein has the nucleotide sequence shown in SEQ ID NO. 1;

the biomaterial is an expression cassette, a vector, a host bacterium, or a host cell that cannot be reproduced as a plant individual.

* * * * *

SEQUENCE LISTING

<160> NUMBER OF SEQ ID NOS: 40

<210> SEQ ID NO 1
<211> LENGTH: 6249
<212> TYPE: DNA
<213> ORGANISM: Artificial Sequence
<220> FEATURE:
<223> OTHER INFORMATION: Synthetic Construct

<400> SEQUENCE: 1

```
aggaaattcg attcactcgt cgacgcgacg ctgctcgcaa gagaaaaaaa gctcccaaat      60
acctccacca ccaccaccac caaagctgcg acgaacacga acggcacaag cacaagagaa     120
agagagagag agagagagag agagagagag agagggagg gagagaggcc ttctcttctc     180
tgctgcggcg gcggcgcatg tgaattgggg tgggatgggt gtgggaggag gcggaggagg     240
aggaggaggg gaggcggcgg cggcggtggc ggtggagggg gatgaggcgg ggaaggggag     300
gaggtggtgg agggtgaagg tgaagctgag cacggtggcg gtggtggcgt gggtgctggc     360
gtcggcggcg ctctgggcgg ggctgcactg gcgcttccgc cgcgcggcgc tgcacaaggc     420
cgaggaggcc ctcgtctgca tgtgcgagga gcgcgcccgc atgctgcagg accagttcgc     480
cgtctccgtc aaccacgtcc acgccctcgc catcctcgtc gccaccttcc actacgacaa     540
gcaccctccc gccctcgacc agtcggccc gaactccgac gagctcttcc gccgccgccg     600
cgatgatcct gttgcatctg ttgttttttt gcccccgcg gttaattgcg ataatgcctc     660
gattttact ccacatcttg cccgtgtact tcgctctgct gcttcttcgg cttcatttaa     720
ttctaccgtg accttccgtg tcagccatgg aagccatgga ttactgttgc tgtctcttgc     780
tattatatgg agcgcacttt ttgttgggag ggagtgaatt gattgtgctt gcttgcttct     840
gttggtagta gtactagtga tttctttggc tgtgtggctg atgaatcttc ttcgatgtgt     900
tgtgcgtgcg tgcgcgtgtg tgcaggacac gttcgccgtg tacgccgcga ggacgtcctt     960
cgagcggccg ctgctgagcg gcgtggcgta cgcgcagcgg gtggtgcacg ccgacaggga    1020
gagcttcgag cggcagcagg ggtggatcat caagaccatg aagcacgagc cgtccccggc    1080
gcaggacgag tacgccccgg tgatctactc ccaggagacc atctcctaca tcgagggcct    1140
cgacgtcatg tccggcgagg tgcgtttctt gggttacagc ttcgcagctg ctgctgcggt    1200
tatcgccatg tccgctgctc tgaactgtgc tgctgggtgt gcttcggcct gcaggaggac    1260
agggagaaca tcttgagggc gagggcgaca gggaaggccg tcctcacgag gccgttccgg    1320
ctgatgtcga atcacttggg tgttgtcttg acgtttcctg tctacctcgt cgatctccca    1380
aatgataccg cggtggagga tcgtgttgct gctactgcag ggtgagggat tactttactt    1440
ttctgaatga agattattct ctccaactga ttcctcttct gtctggaatc cactgccttc    1500
agctcttcgt tttgttgcag tcgttgttgg atgcttttag tagtggaaat gtgtgcgttt    1560
cagggatatt tgatcacatg caacattttc actcataact ggctgaaaaa gttttgcatt    1620
aatagagctg aaatgtctag atggataagc aattgcagtg gtattttaag tacaacatgt    1680
gcaacgaatg gctccattta acttttttct tttgttcggc agataccttg gaggagcatt    1740
tgatgtggag tcactagtag aaaatttgtt gagacagtta gctggtaacc aggaattggt    1800
ggtcaatgtt tatgatgtca caaaccactc aaaccctctt gtgatgtatg atctgaggt    1860
tcctcttggt attccctcac catcacacac ctatacgttg gattttggtg atccattgag    1920
aaagcatcag atggtttgca ggtaaatttg tgtgaattga tcgttggttt tcccatttta    1980
tattatagaa cgatcggttt ttttaacatc cattggccat aaatctgagc agatacagaa    2040
```

```
acaagcttca tgtttcatgg tctgcaatta ctacaccatc aggggtcttt gttatatgta    2100
tgctggtggg ctacataata tatgctgctt ggagtcgcta cgataatgtt aaggaagatt    2160
gccggaaaat ggaagcgctg aaaaaacggg cagaagcggc tgatattgct aaatctcagg    2220
tatagttgga tgttgtttgc ttctctattt ctattgcaag cttattgtta tatctaaaag    2280
gttcttattc atttatgaca gttccttgca actgtttctc atgagatcag aacacccatg    2340
aatggcgtgc tgggtatttt ctttgatctt acaacacatt cagtttaatg ttatgcaact    2400
catttctttt gaaaaatgga atcatctct ttgtttcttt tccctaggaa tgcttgatat    2460
gttattagac acagagctga agtcaaccca gagggattat gcacaaacag cccaagtctg    2520
tggaaaggca ttaatatccc tgattaacga agtgcttgac agggccaaaa tcgaggctgg    2580
caagatagat ctcgagtcag taccatttga cctgaggtcc atccttgatg atgtcatctc    2640
gttattttct tcaaaatcaa gagagaaagg aattgaggtt agttaaactg atttcggtca    2700
tggttggaca aagatcacta aacgtattaa gtttctgcca gccatcaatt atttctttta    2760
ggaaaatatc atgcactagt tccaccgaca tcttttagtc tcttagcttg atactctttc    2820
catgaacttc tctgcattac cgtcatgcac catgcacgtt taactttgtt taatcccagt    2880 tgatttttctt ctatgttgta acttccagct tgctgtatat gtttctgaaa gagttcctga    2940
aatcctgttg ggcgaccctg gaaggtttcg tcagataatt acaaacttgg tgggaaactc    3000
gatcaaggta aatgcgcata acctttgtat ccattcatga ttttctttaa cgataccaat    3060
agttctcacc aatgacatca ggcaacttgt ttcttagtat actattgttc aatgtgaaca    3120
caagataaca atatttacct tgtcgcagtt cacagaacgg gggcacattt ttgtacaagt    3180
tcacctggca gatcactcaa atcttgcaac agaagcaaaa attgaaccag tagtcaatgg    3240
gatgaatgga cataaagacg aggctattgc tatacccacc agtgggtctc ataacacttt    3300
aagtggtttt gaagcagctg atagccgaaa taactgggaa aacttcaagc ttttgctctc    3360
ttacgagaaa aatgaaatgc catatgaaag tgattctgat aaagtaactc ttgttgttag    3420
tgtggaagat actgggatag gcataccact gcatgcccaa ggccgggtct tcacgccttt    3480
catgcaagct gacagctcaa cttctaggaa ctatggtgga actggcattg gattgagcat    3540
cagcaaatgt cttgttgaaa taatgggtgg tcagataaac tttgtcagcc gacctcttgt    3600
tgggagcaca ttcacattca ctgctgttct gagaaggtgt gacaaaaatg ctattagtga    3660
cagtaagact gttgctttgc acccattacc gtccagtttt aaaggcttat ctgcgctatt    3720
ggttgataaa agacctgtaa gagcaactgt gactaagtat catttgcaaa ggcttggaat    3780
cacttctgaa gttgttggta ccattgatcc gacatttggt gtgttgtctg ggagaaatgg    3840
cagttctcta accaggtact tctatcttct acattccttt caaaaaattg aaatcctgga    3900
gttaataggc tacttttctc tggaaattag aataaacgga gcatgcttgc atactaactt    3960
cttatgcaaa tatcactgtt ctatgtataa atgattacac gataatgatt gttttttggt    4020
aagtattact gggtaatact tggccatcat agttcttgcc tttattttgt atcacttcgg    4080
tatattgcta cttctgcggc agttctcttt acgctaccga atgtgatata tttaattgaa    4140
aattgatttt atttaatct gtgaaaagaa cattttttta aggccccaca attctcaaat    4200
aactagtaag ctgattgcag atgatatttg aactatcttg acacccagtt ttttttttta    4260
atctaactcg ttttgttcca aatttgttgt cagcattggt aagaagcagc catgcatgtt    4320
gctaatcgag agtgattcct ggggaccaca gatggatgtc tccttacatg ctagacttca    4380
```

-continued

| | |
|---|---|
| ggagatgaaa cagagtgatc gcatacatgt attgcccaag gttttccttc tttctgctgc | 4440 |
| agaatcagac aaagtaaaga agatacatgc agttgattct gtgataccaa agcctctgaa | 4500 |
| agcaagtgca cttgcggcct gtctgttcca agcacttggt atcacacagc cgagccatga | 4560 |
| gaaacgtgac gattcaggtt ctcttcatgg gcgtgatggt tcaggttctc ttcatgggtt | 4620 |
| gcttcttggc aagaacatat tggtagttga tgacaacaag gtaaacctca gagtggccgc | 4680 |
| tggtacattg aagaaatatg gggcaaaggt ggagtgtgtg gagagtggaa agatgctct | 4740 |
| ttcccttcta caagtgccgc acaagtttga tctgtgtctc atggacattc agatgccgga | 4800 |
| gatggatggg taagcttatg tcccgttcaa gatttatttc ttttgaattt gagcctttta | 4860 |
| tttcatatga tccaaagcgt gacatgtcat ctggataagt gccacctcgt tgactatcaa | 4920 |
| tttattcacg caatgaatca ggctttctgc ctctttttga agaaaaaaaa aatgttattc | 4980 |
| acacttcgtg gttaatggaa acaagcatat acattgctga cgccaaatac tgattataac | 5040 |
| tagtaaaaat gtcagtcttg tgttagtttt ttatgtgcga aaaatgccgt gtctaattca | 5100 |
| ttatgtgaaa attttcaaag acattagccc tgatatcgtc ctgcattatg ccaaacagta | 5160 |
| ctttaaatat taatatcaga aggtctaaaa tccgtgcagt taccatttgt tcattgtagt | 5220 |
| tttaaccatc atactgcaat atgcagttct tgggctaatg aacataatgg tgtgctaaca | 5280 |
| ccctcatgac caattaactt atgtctcttg aacacttgct gcatattgac atctctgttc | 5340 |
| ctatattttc tgaatagtaa ccaagtaatg tcaaaccatg tcattatttt gtcttcgttt | 5400 |
| aatcaacata gttttgcttc atgtgctaga tttgaggcaa ctcggcaaat acgagcaatg | 5460 |
| gaagggaagg caaatgagca ggcagacgac agcgaatcgg gttcagaaat cgcagcaaag | 5520 |
| acggccaaat ggcacttgcc aatcctggca atgaccgctg atgtcatcca ggccacccac | 5580 |
| gaggaatgca caaagtgcgg gatggatggc tacgtctcga agcctttga ggagaagcag | 5640 |
| ctcttccagg cagtacagaa gttcttgggc ccatgcgttt ccagctgaca ccaaccgatg | 5700 |
| cattctgctg tacaccaaga gagtaaagaa tgagcactga ctgtgaactg aggcggctaa | 5760 |
| aattcttctc cattttgttg ctcttcaaca gaggatgcga tctgaatgag agcctgcact | 5820 |
| caaggcgaca ttgcacagaa aggatcggag ccttcattgt gtacatgtat ttttatcggc | 5880 |
| agagaccaag agctatagtt ttaagctagg agaagcataa gttttagggt gacatgtccg | 5940 |
| gcctcctgtt atcggagcca caggtgtgtt gctgggctat tggaatcttg agcaattttt | 6000 |
| ttttcctgta cagctcccac gattttcgg ctccagccca ctgttgacag aagacatgtt | 6060 |
| tgcagggtgc agcatcttgg aaaaacctga taacctgaga attttttgtt gtgtcattct | 6120 |
| gtgtgcagta tattagaatt tgagcagtat tgtatatcaa tgtaccatcg gtgtatggat | 6180 |
| gtgaacaagg aaggcgaaac ctgtgattag gacactgatt aaaacttgca ctcgtttttt | 6240 |
| ccatcccgt | 6249 |

<210> SEQ ID NO 2
<211> LENGTH: 8802
<212> TYPE: DNA
<213> ORGANISM: Artificial Sequence
<220> FEATURE:
<223> OTHER INFORMATION: Synthetic Construct

<400> SEQUENCE: 2

| | |
|---|---|
| cgtgaacaat gtctacgtag gagggccaac gaccttgata cgattctgat atacatagta | 60 |
| cgtgagacag tacgcaagtt ggcaaagtca atgtgtacaa aaaaaaaaaa ggaactaaac | 120 |
| aatgggatcc gatccggtcg gaccgaacag tacgttggct gtggttagct atattaatac | 180 |

```
agccttaacc cacagtgatc cgttgtttaa tcggttactt aggcatgtgg cctaaaccag    240
acacacgcat gcatgcgccg cgtcaaaaat aatgtgaaca gatgcttgta ctgtgtagtg    300
cgtgctaatg tgccatttat tattttttat tttcttcacc tttttcgcta taaaaaaatt    360
taaaaaacag tgctcgtgct gcctgatgat cagttctgcc gtgttttcgg agcagaaagt    420
gataaataat tctccagcta attaatgatt gaccttacac ctatttatgc tgctggaact    480
aatgatttgg atcagcttaa aaatagctta aaaattggtt actactataa cacacagttg    540
gtggctgatg agatcgtctc gaatcgccat caaaacgagc ttacgcctcc gaaagctgtg    600
acacgtagtc actgactgct gctccattac gttgcaacta ttcacaaacc tcaaaagaaa    660
aatttgaaaa acaagaatag ccgctaatga acccatgtg ctcgcagaga caagataaca    720
aacaacgaga aaaaaaaggc aattgtgttt atccttttc cgtaagaaa gatcagtgat    780 cgcaacaacg agcaaaaagg catcgtgttt atctcacttt ttttcctttc ctgtaaaaag    840
gtttaggctg tggttagatc cttagccaat tttttaagt atactagcac acatttaaag    900
tattaaacgt agactaataa caaaacaaat tacagattcc gtctgtaaac tgtgagacga    960
atttattaag cctaattaat tcgtcattag taaatgttta ctgtagcatc acattatcaa   1020
atcattgcgt aattaagctt aaaagattcg tctcataatt tatatgtaaa ctatgtaatt   1080
ggttttttcg ttcatatcta atacttcata catgtgtcaa atatttaatg tgatattttt   1140
taaaaaaaaa ttaaatctaa aaacggcctc agtgctatcg tagcagaaaa gtaaatcggg   1200
cgagatttgt ccgatgcctg tgacagatgg agacagcatt gttgaccaca ctctctattg   1260
aaaaaaaaac aactactgat tatgtatcca gatacatagc ccataattgt ttttctccaa   1320
aaaaatgtat tgatgcatca gtgtcttcta tccaattata aacagattgt tataatagtt   1380
tatctagaca gttataacac atacaatcaa tacttgaata aacaaattta acaaacagta   1440
ataaccaaac gatctaattg caatgtaaat aggaaaagtt tagagttgga ataattatt   1500 aaaaatagggt agaattaaac tgagagagat tgtgattagt tgataagtga agatacgtga   1560
ctcatgattg attagtaaaa aaatactggt ggagaaatta ttatatttta agctaaattt   1620
tactacacca tattttaatg tataacgctg ttaactttta attaaacgtt taaccattcg   1680
tattattcaa aaaatttatg taattatcat ttattttatt atgacttgat tcgtcatcaa   1740
atgtccttta agcatgacat aaaaatatga atgatcaaac gttaaataaa ataaatgatt   1800
aaacgttaat aaaaaagtca acggtgtcat acgaaataaa aagctaagaa acggaaata   1860 gttaaaaaca agacgggacc acgtgggccc ccacctgcca ggatttgccc cgacccacac   1920
agccgggtgc cagtgccagg caagccgcca aaggcacaag gcacggcgat ccaagcaaac   1980
cgaaccacag ctcgctcaac cactgcccgc ccggtcgcga ccgcgcgatc cgatccccca   2040
gccgaaccac ctccccggag gcggtcggcc cggctggctg gccgcgcggc gcgcctgggc   2100
gccagcggcg tgtcgccgc ggtggtggtg ggatagggga ggaaagcaac ggggcaccag   2160
ctgaccagca gcggcggcgt caggggggcgg ggcggagccg caaaaaggcg ggaggcccgt   2220
gggccccgcc ggcgaggtgg gggcgaaaga ggaaaaaaaa gataaaaata aatcccggtt   2280
attttaaggc gcggcgtatc tcgggaaatc caggaaattc gattcactcg tcgacgcgac   2340
gctgctcgca agagaaaaaa agctcccaaa tacctccacc accaccacca ccaaagctgc   2400
gacgaacacg aacggcacaa gcacaagaga aagagagaga gagagagaga gagagagaga   2460
gagaggggag ggagagaggc cttctcttct ctgctgcggc ggcggcgcat gtgaattggg   2520
```

-continued

```
gtgggatggg tgtgggagga ggcggaggag gaggaggagg ggaggcggcg gcggcggtgg    2580
cggtggaggg ggatgaggcg gggaagggga ggaggtggtg gagggtgaag gtgaagctga    2640
gcacggtggc ggtggtggcg tgggtgctgg cgtcggcggc gctctgggcg gggctgcact    2700
ggcgcttccg ccgcgcggcg ctgcacaagg ccgaggaggc cctcgtctgc atgtgcgagg    2760
agcgcgcccg catgctgcag gaccagttcg ccgtctccgt caaccacgtc cacgccctcg    2820
ccatcctcgt cgccaccttc cactacgaca agcaccctcc cgcccgcgac caggtcggcc    2880
cgaactccga cgagctcttc cgccgccgcc gcgatgatcc tgttgcatct gttgtttttt    2940
tgccccccgc ggttaattgc gataatgcct cgattttttac tccacatctt gcccgtgtac    3000
ttcgctctgc tgcttcttcg gcttcattta attctaccgt gaccttccgt gtcagccatg    3060
gaagccatgg attactgttg ctgtctcttg ctattatatg gagcgcactt tttgttggga    3120
gggagtgaat tgattgtgct tgcttgcttc tgttggtagt agtactagtg atttctttgg    3180
ctgtgtggct gatgaatctt cttcgatgtg ttgtgcgtgc gtgcgcgtgt gtgcaggaca    3240
cgttcgccgt gtacgccgcg aggacgtcct tcgagcggcc gctgctgagc ggcgtggcgt    3300
acgcgcagcg ggtggtgcac gccgacaggg agagcttcga gcggcagcag gggtggatca    3360
tcaagaccat gaagcacgag ccgtccccg cgcaggacga gtacgccccg gtgatctact    3420
cccaggagac catctcctac atcgagggcc tcgacgtcat gtccggcgag gtgcgtttct    3480
tgggttacag cttcgcagct gctgctgcgg ttatcgccat gtccgctgct ctgaactgtg    3540
ctgctgggtg tgcttcggcc tgcaggagga cagggagaac atcttgaggg cgagggcgac    3600
agggaaggcc gtcctcacga ggccgttccg gctgatgtcg aatcacttgg gtgttgtctt    3660
gacgtttcct gtctacctcg tcgatctccc aaatgatacc gcggtggagg atcgtgttgc    3720
tgctactgca gggtgaggga ttactttact tttctgaatg aagattattc tctccaactg    3780
attcctcttc tgtctggaat ccactgcctt cagctcttcg ttttgttgca gtcgttgttg    3840
gatgctttta gtagtggaaa tgtgtgcgtt tcagggatat ttgatcacat gcaacatttt    3900
cactcataac tggctgaaaa agttttgcat taatagagct gaaatgtcta gatggataag    3960
caattgcagt ggtatttttaa gtacaacatg tgcaacgaat ggctccattt aacttttttct    4020 ttttgttcgg cagatacctt ggaggagcat ttgatgtgga gtcactagta gaaaatttgt    4080
tgagacagtt agctggtaac caggaattgg tggtcaatgt ttatgatgtc acaaaccact    4140
caaaccctct tgtgatgtat ggatctgagg ttcctcttgg tattccctca ccatcacaca    4200
cctatacgtt ggattttggt gatccattga gaaagcatca gatggtttgc aggtaaattt    4260
gtgtgaattg atcgttggtt ttcccatttt atattataga acgatcggtt ttttttaacat    4320 ccattggcca taaatctgag cagatacaga aacaagcttc atgtttcatg gtctgcaatt    4380
actacaccat cagggtgtctt tgttatatgt atgctggtgg gctacataat atatgctgct    4440
tggagtcgct acgataatgt taaggaagat tgccggaaaa tggaagcgct gaaaaaacgg    4500
gcagaagcgg ctgatattgc taaatctcag gtatagttgg atgttgtttg cttctctatt    4560
tctattgcaa gcttattgtt atatctaaaa ggttcttatt catttatgac agttccttgc    4620
aactgtttct catgagatca gaacacccat gaatggcgtg ctgggtattt tctttgatct    4680
tacaacacat tcagtttaat gttatgcaac tcatttcttt tgaaaaaatg gaatcatctc    4740 tttgttctt ttccctagga atgcttgata tgttattaga cacagagctg aagtcaaccc    4800
agagggatta tgcacaaaca gcccaagtct gtggaaaggc attaatatcc ctgattaacg    4860
aagtgcttga cagggccaaa atcgaggctg gcaagataga tctcgagtca gtaccatttg    4920
```

-continued

```
acctgaggtc catccttgat gatgtcatct cgttatttto ttcaaaatca agagagaaag    4980
gaattgaggt tagttaaact gatttcggtc atggttggac aaagatcact aaacgtatta    5040
agtttctgcc agccatcaat tatttctttt aggaaaatat catgcactag ttccaccgac    5100
atcttttagt ctcttagctt gatactcttt ccatgaactt ctctgcatta ccgtcatgca    5160
ccatgcacgt ttaactttgt ttaatcccag ttgattttct tctatgttgt aacttccagc    5220
ttgctgtata tgtttctgaa agagttcctg aaatcctgtt gggcgaccct ggaaggtttc    5280
gtcagataat tacaaacttg gtgggaaact cgatcaaggt aaatgcgcat aacctttgta    5340
tccattcatg attttcttta acgataccaa tagttctcac caatgacatc aggcaacttg    5400
tttcttagta tactattgtt caatgtgaac acaagataac aatatttacc ttgtcgcagt    5460
tcacagaacg ggggcacatt tttgtacaag ttcacctggc agatcactca aatcttgcaa    5520
cagaagcaaa aattgaacca gtagtcaatg ggatgaatgg acataaagac gaggctattg    5580 ctataccccac cagtgggtct cataacactt taagtggttt tgaagcagct gatagccgaa    5640
ataactggga aaacttcaag cttttgctct cttacgagaa aaatgaaatg ccatatgaaa    5700
gtgattctga taaagtaact cttgttgtta gtgtggaaga tactgggata ggcataccac    5760
tgcatgccca aggccgggtc ttcacgcctt tcatgcaagc tgacagctca acttctagga    5820
actatggtgg aactggcatt ggattgagca tcagcaaatg tcttgttgaa ataatgggtg    5880
gtcagataaa ctttgtcagc cgacctcttg ttgggagcac attcacattc actgctgttc    5940
tgagaaggtg tgacaaaaat gctattagtg acagtaagac tgttgctttg cacccattac    6000
cgtccagttt taaaggctta tctgcgctat tggttgataa aagacctgta agagcaactg    6060
tgactaagta tcatttgcaa aggcttggaa tcacttctga agttgttggt accattgatc    6120
cgacatttgg tgtgttgtct gggagaaatg gcagttctct aaccaggtac ttctatcttc    6180
tacattcctt tcaaaaaatt gaaatcctgg agttaatagg ctacttttct ctggaaatta    6240
gaataaacgg agcatgcttg catactaact tcttatgcaa atatcactgt tctatgtata    6300
aatgattaca cgataatgat tgttttttgg taagtattac tgggtaatac ttggccatca    6360
tagttcttgc ctttattttg tatcacttcg gtatattgct acttctgcgg cagttctctt    6420
tacgctaccg aatgtgatat atttaattga aaattgattt tatttttaatc tgtgaaaaga    6480 acatttttt aaggccccac aattctcaaa taactagtaa gctgattgca gatgatattt    6540
gaactatctt gacacccagt ttttttttt aatctaactc gttttgttcc aaatttgttg    6600
tcagcattgg taagaagcag ccatgcatgt tgctaatcga gagtgattcc tggggaccac    6660
agatggatgt ctccttacat gctagacttc aggagatgaa acagagtgat cgcatacatg    6720
tattgcccaa ggttttcctt ctttctgctg cagaatcaga caaagtaaag aagatacatg    6780
cagttgattc tgtgatacca aagcctctga agcaagtgc acttgcggcc tgtctgttcc    6840
aagcacttgg tatcacacag ccgagccatg agaaacgtga cgattcaggt tctcttcatg    6900
ggcgtgatgg ttcaggttct cttcatgggt tgcttcttgg caagaacata ttggtagttg    6960
atgacaacaa ggtaaacctc agagtggccg ctggtacatt gaagaaatat ggggcaaagg    7020
tggagtgtgt ggagagtgga aaagatgctc tttcccttct acagtgccg cacaagtttg    7080 atctgtgtct catggacatt cagatgccgg agatggatgg gtaagcttat gtcccgttca    7140
agatttattt ctttttgaatt tgagcctttt atttcatatg atccaaagcg tgacatgtca    7200
tctggataag tgccacctcg ttgactatca atttattcac gcaatgaatc aggctttctg    7260
```

-continued

| | |
|---|---|
| cctctttttg aagaaaaaaa aaatgttatt cacacttcgt ggttaatgga aacaagcata | 7320 |
| tacattgctg acgccaaata ctgattataa ctagtaaaaa tgtcagtctt gtgttagttt | 7380 |
| tttatgtgcg aaaaatgccg tgtctaattc attatgtgaa aattttcaaa gacattagcc | 7440 |
| ctgatatcgt cctgcattat gccaaacagt actttaaata ttaatatcag aaggtctaaa | 7500 |
| atccgtgcag ttaccatttg ttcattgtag ttttaaccat catactgcaa tatgcagttc | 7560 |
| ttgggctaat gaacataatg gtgtgctaac accctcatga ccaattaact tatgtctctt | 7620 |
| gaacacttgc tgcatattga catctctgtt cctatatttt ctgaatagta accaagtaat | 7680 |
| gtcaaaccat gtcattattt tgtcttcgtt taatcaacat agttttgctt catgtgctag | 7740 |
| atttgaggca actcggcaaa tacgagcaat ggaagggaag gcaaatgagc aggcagacga | 7800 |
| cagcgaatcg ggttcagaaa tcgcagcaaa gacggccaaa tggcacttgc caatcctggc | 7860 |
| aatgaccgct gatgtcatcc aggccaccca cgaggaatgc acaaagtgcg ggatggatgg | 7920 |
| ctacgtctcg aagccctttg aggagaagca gctcttccag gcagtacaga agttcttggg | 7980 |
| cccatgcgtt tccagctgac accaaccgat gcattctgct gtacaccaag agagtaaaga | 8040 |
| atgagcactg actgtgaact gaggcggcta aaattcttct ccatttttgtt gctcttcaac | 8100 |
| agaggatgcg atctgaatga gagcctgcac tcaaggcgac attgcacaga aaggatcgga | 8160 |
| gccttcattg tgtacatgta tttttatcgg cagagaccaa gagctatagt tttaagctag | 8220 |
| gagaagcata agttttaggg tgacatgtcc ggcctcctgt tatcggagcc acaggtgtgt | 8280 |
| tgctgggcta ttggaatctt gagcaatttt ttttcctgt acagctccca cgatttttcg | 8340 |
| gctccagccc actgttgaca gaagacatgt ttgcagggtg cagcatcttg aaaaacctg | 8400 |
| ataacctgag aatttttttgt tgtgtcattc tgtgtgcagt atattagaat ttgagcagta | 8460 |
| ttgtatatca atgtaccatc ggtgtatgga tgtgaacaag gaaggcgaaa cctgtgatta | 8520 |
| ggacactgat taaaacttgc actcgttttt tccatcccgt acagaatatg tatcaagcag | 8580 |
| tgcatttata tgcagaatac tttgccatga agcggaaatg atgagagagc gctcgttgga | 8640 |
| attttgggaa gccacagctt ctgctcaaac tcggccgacg ggcaaagggc attcactgaa | 8700 |
| acattggcat attagtacag tactacggaa aagtataccg aagtcccctc aacattggca | 8760 |
| tattagtaca atactaggga gtactatgct gtaggctggt ag | 8802 |

<210> SEQ ID NO 3
<211> LENGTH: 3018
<212> TYPE: DNA
<213> ORGANISM: Artificial Sequence
<220> FEATURE:
<223> OTHER INFORMATION: Synthetic Construct

<400> SEQUENCE: 3

| | |
|---|---|
| atgggtgtgg gaggaggcgg aggaggagga ggaggggagg cggcggcggc ggtggcggtg | 60 |
| gagggggatg aggcggggaa ggggaggagg tggtggaggg tgaaggtgaa gctgagcacg | 120 |
| gtggcggtgg tggcgtgggt gctggcgtcg gcggcgctct gggcggggct gcactggcgc | 180 |
| ttccgccgcg cggcgctgca caaggccgag gaggccctcg tctgcatgtg cgaggagcgc | 240 |
| gcccgcatgc tgcaggacca gttcgccgtc tccgtcaacc acgtccacgc cctcgccatc | 300 |
| ctcgtcgcca ccttccacta cgacaagcac cctcccgccc tcgaccagga cacgttcgcc | 360 |
| gtgtacgccc cgaggacgtc cttcgagcgg ccgctgctga gcggcgtggc gtacgcgcag | 420 |
| cgggtggtgc acgccgacag ggagagcttc gagcggcagc aggggtggat catcaagacc | 480 |
| atgaagcacg agccgtcccc ggcgcaggac gagtacgccc cggtgatcta ctcccaggag | 540 |

```
accatctcct acatcgaggg cctcgacgtc atgtccggcg aggaggacag ggagaacatc    600
ttgagggcga gggcgacagg gaaggccgtc ctcacgaggc cgttccggct gatgtcgaat    660
cacttgggtg ttgtcttgac gtttcctgtc tacctcgtcg atctcccaaa tgataccgcg    720
gtggaggatc gtgttgctgc tactgcagga taccttggag gagcatttga tgtggagtca    780
ctagtagaaa atttgttgag acagttagct ggtaaccagg aattggtggt caatgtttat    840
gatgtcacaa accactcaaa ccctcttgtg atgtatggat ctgaggttcc tcttggtatt    900
ccctcaccat cacacaccta tacgttggat tttggtgatc cattgagaaa gcatcagatg    960
gtttgcagat acagaaacaa gcttcatgtt tcatggtctg caattactac accatcaggg   1020
gtctttgtta tatgtatgct ggtgggctac ataatatatg ctgcttggag tcgctacgat   1080
aatgttaagg aagattgccg gaaaatggaa gcgctgaaaa acgggcaga gcggctgat    1140 attgctaaat ctcagttcct tgcaactgtt tctcatgaga tcagaacacc catgaatggc   1200
gtgctgggaa tgcttgatat gttattagac acagagctga agtcaaccca gagggattat   1260
gcacaaacag cccaagtctg tggaaaggca ttaatatccc tgattaacga agtgcttgac   1320
agggccaaaa tcgaggctgg caagatagat ctcgagtcag taccatttga cctgaggtcc   1380
atccttgatg atgtcatctc gttatttcct tcaaaatcaa gagagaaagg aattgagctt   1440
gctgtatatg tttctgaaag agttcctgaa atcctgttgg gcgaccctgg aaggtttcgt   1500
cagataatta caaacttggt gggaaactcg atcaagttca cagaacgggg gcacattttt   1560
gtacaagttc acctggcaga tcactcaaat cttgcaacag aagcaaaaat tgaaccagta   1620
gtcaatggga tgaatggaca taaagacgag gctattgcta tacccaccag tgggtctcat   1680
aacactttaa gtggttttga agcagctgat agccgaaata actgggaaaa cttcaagctt   1740
ttgctctctt acgagaaaaa tgaaatgcca tatgaaagtg attctgataa agtaactctt   1800
gttgttagtg tggaagatac tgggataggc ataccactgc atgcccaagg ccgggtcttc   1860
acgcctttca tgcaagctga cagctcaact tctaggaact atggtggaac tggcattgga   1920
ttgagcatca gcaaatgtct tgttgaaata atgggtggtc agataaactt tgtcagccga   1980
cctcttgttg ggagcacatt cacattcact gctgttctga aaggtgtgta caaaaatgct   2040
attagtgaca gtaagactgt tgcttttgcac ccattaccgt ccagttttaa aggcttatct   2100
gcgctattgg ttgataaaag acctgtaaga gcaactgtga ctaagtatca tttgcaaagg   2160
cttggaatca cttctgaagt tgttggtacc attgatccga catttggtgt gttgtctggg   2220
agaaatggca gttctctaac cagcattggt aagaagcagc catgcatgtt gctaatcgag   2280
agtgattcct ggggaccaca gatggatgtc tccttacatg ctagacttca ggagatgaaa   2340
cagagtgatc gcatacatgt attgcccaag gttttccttc tttctgctgc agaatcagac   2400
aaagtaaaga agatacatgc agttgattct gtgataccaa agcctctgaa agcaagtgca   2460
cttgcggcct gtctgttcca agcacttggt atcacacagc cgagccatga gaaacgtgac   2520
gattcaggtt ctcttcatgg gcgtgatggt tcaggttctc ttcatggggtt gcttcttggc   2580 aagaacatat tggtagttga tgacaacaag gtaaacctca gagtggccgc tggtacattg   2640
aagaaatatg gggcaaaggt gggagtgtgtg gagagtggaa aagatgctct ttcccttcta   2700
caagtgccgc acaagtttga tctgtgtctc atggacattc agatgccgga gatggatgga   2760
tttgaggcaa ctcggcaaat acgagcaatg gaagggaagg caaatgagca ggcagacgac   2820
agcgaatcgg gttcagaaat cgcagcaaag acggccaaat ggcacttgcc aatcctggca   2880
```

-continued

```
atgaccgctg atgtcatcca ggccacccac gaggaatgca caaagtgcgg gatggatggc    2940
tacgtctcga agcccttga ggagaagcag ctcttccagg cagtacagaa gttcttgggc     3000
ccatgcgttt ccagctga                                                   3018
```

<210> SEQ ID NO 4
<211> LENGTH: 1013
<212> TYPE: PRT
<213> ORGANISM: Artificial Sequence
<220> FEATURE:
<223> OTHER INFORMATION: Synthetic Construct

<400> SEQUENCE: 4

```
Met Gly Val Gly Gly Gly Gly Gly Gly Gly Gly Glu Ala Ala Ala
1               5                   10                  15

Ala Val Ala Val Glu Gly Asp Glu Ala Gly Lys Gly Arg Arg Trp Trp
            20                  25                  30

Arg Val Lys Val Lys Leu Ser Thr Val Ala Val Ala Trp Val Leu
        35                  40                  45

Ala Ser Ala Ala Leu Trp Ala Gly Leu His Trp Arg Phe Arg Arg Ala
    50                  55                  60

Ala Leu His Lys Ala Glu Glu Ala Leu Val Cys Met Cys Glu Arg
65                  70                  75                  80

Ala Arg Met Leu Gln Asp Gln Phe Ala Val Ser Val Asn His Val His
                85                  90                  95

Ala Leu Ala Ile Leu Val Ala Thr Phe His Tyr Asp Lys His Pro Pro
            100                 105                 110

Ala Leu Asp Gln Asp Thr Phe Ala Val Tyr Ala Ala Arg Thr Ser Phe
        115                 120                 125

Glu Arg Pro Leu Leu Ser Gly Val Ala Tyr Ala Gln Arg Val Val His
    130                 135                 140

Ala Asp Arg Glu Ser Phe Glu Arg Gln Gln Gly Trp Ile Ile Lys Thr
145                 150                 155                 160

Met Lys His Glu Pro Ser Pro Ala Gln Asp Glu Tyr Ala Pro Val Ile
                165                 170                 175

Tyr Ser Gln Glu Thr Ile Ser Tyr Ile Glu Gly Leu Asp Val Met Ser
            180                 185                 190

Gly Glu Glu Asp Arg Glu Asn Ile Leu Arg Ala Arg Ala Thr Gly Lys
        195                 200                 205

Ala Val Leu Thr Arg Pro Phe Arg Leu Met Ser Asn His Leu Gly Val
    210                 215                 220

Val Leu Thr Phe Pro Val Tyr Leu Val Asp Leu Pro Asn Asp Thr Ala
225                 230                 235                 240

Val Glu Asp Arg Val Ala Ala Thr Ala Gly Tyr Leu Gly Gly Ala Phe
                245                 250                 255

Asp Val Glu Ser Leu Val Glu Asn Leu Leu Arg Gln Leu Ala Gly Asn
            260                 265                 270

Gln Glu Leu Val Val Asn Val Tyr Asp Val Thr Asn His Ser Asn Pro
        275                 280                 285

Leu Val Met Tyr Gly Ser Glu Val Pro Leu Gly Ile Pro Ser Pro Ser
    290                 295                 300

His Thr Tyr Thr Leu Asp Phe Gly Asp Pro Leu Arg Lys His Gln Met
305                 310                 315                 320

Val Cys Arg Tyr Arg Asn Lys Leu His Val Ser Trp Ser Ala Ile Thr
                325                 330                 335
```

-continued

```
Thr Pro Ser Gly Val Phe Val Ile Cys Met Leu Val Gly Tyr Ile Ile
            340                 345                 350

Tyr Ala Ala Trp Ser Arg Tyr Asp Asn Val Lys Glu Asp Cys Arg Lys
        355                 360                 365

Met Glu Ala Leu Lys Lys Arg Ala Glu Ala Asp Ile Ala Lys Ser
    370                 375                 380

Gln Phe Leu Ala Thr Val Ser His Glu Ile Arg Thr Pro Met Asn Gly
385                 390                 395                 400

Val Leu Gly Met Leu Asp Met Leu Leu Asp Thr Glu Leu Lys Ser Thr
                405                 410                 415

Gln Arg Asp Tyr Ala Gln Thr Ala Gln Val Cys Gly Lys Ala Leu Ile
            420                 425                 430

Ser Leu Ile Asn Glu Val Leu Asp Arg Ala Lys Ile Glu Ala Gly Lys
        435                 440                 445

Ile Asp Leu Glu Ser Val Pro Phe Asp Leu Arg Ser Ile Leu Asp Asp
    450                 455                 460

Val Ile Ser Leu Phe Ser Ser Lys Ser Arg Glu Lys Gly Ile Glu Leu
465                 470                 475                 480

Ala Val Tyr Val Ser Glu Arg Val Pro Glu Ile Leu Leu Gly Asp Pro
                485                 490                 495

Gly Arg Phe Arg Gln Ile Ile Thr Asn Leu Val Gly Asn Ser Ile Lys
            500                 505                 510

Ile Thr Ile Phe Thr Leu Ser Gln Phe Thr Glu Arg Gly His Ile Phe
        515                 520                 525

Val Gln Val His Leu Ala Asp His Ser Asn Leu Ala Thr Glu Ala Lys
    530                 535                 540

Ile Glu Pro Val Val Asn Gly Met Asn Gly His Lys Asp Glu Ala Ile
545                 550                 555                 560

Ala Ile Pro Thr Ser Gly Ser His Asn Thr Leu Ser Gly Phe Glu Ala
                565                 570                 575

Ala Asp Ser Arg Asn Asn Trp Glu Asn Phe Lys Leu Leu Leu Ser Tyr
            580                 585                 590

Glu Lys Asn Glu Met Pro Tyr Glu Ser Asp Ser Asp Lys Val Thr Leu
        595                 600                 605

Val Val Ser Val Glu Asp Thr Gly Ile Gly Ile Pro Leu His Ala Gln
    610                 615                 620

Gly Arg Val Phe Thr Pro Phe Met Gln Ala Asp Ser Ser Thr Ser Arg
625                 630                 635                 640

Asn Tyr Gly Gly Thr Gly Ile Gly Leu Ser Ile Ser Lys Cys Leu Val
                645                 650                 655

Glu Ile Met Gly Gly Gln Ile Asn Phe Val Ser Arg Pro Leu Val Gly
            660                 665                 670

Ser Thr Phe Thr Phe Thr Ala Val Leu Arg Arg Cys Asp Lys Asn Ala
        675                 680                 685

Ile Ser Asp Ser Lys Thr Val Ala Leu His Pro Leu Pro Ser Ser Phe
    690                 695                 700

Lys Gly Leu Ser Ala Leu Leu Val Asp Lys Arg Pro Val Arg Ala Thr
705                 710                 715                 720

Val Thr Lys Tyr His Leu Gln Arg Leu Gly Ile Thr Ser Glu Val Val
                725                 730                 735

Gly Thr Ile Asp Pro Thr Phe Gly Val Leu Ser Gly Arg Asn Gly Ser
            740                 745                 750

Ser Leu Thr Ser Ile Gly Lys Lys Gln Pro Cys Met Leu Leu Ile Glu
```

-continued

|     |     |     | 755 |     |     |     | 760 |     |     |     | 765 |     |
|---|---|---|---|---|---|---|---|---|---|---|---|---|

Ser Asp Ser Trp Gly Pro Gln Met Asp Val Ser Leu His Ala Arg Leu
    770                  775                  780

Gln Glu Met Lys Gln Ser Asp Arg Ile His Val Leu Pro Lys Val Phe
785                  790                  795                  800

Leu Leu Ser Ala Ala Glu Ser Asp Lys Val Lys Lys Ile His Ala Val
            805                  810                  815

Asp Ser Val Ile Pro Lys Pro Leu Lys Ala Ser Ala Leu Ala Ala Cys
        820                  825                  830

Leu Phe Gln Ala Leu Gly Ile Thr Gln Pro Ser His Glu Lys Arg Asp
            835                  840                  845

Asp Ser Gly Ser Leu His Gly Arg Asp Gly Ser Gly Ser Leu His Gly
        850                  855                  860

Leu Leu Leu Gly Lys Asn Ile Leu Val Val Asp Asp Asn Lys Val Asn
865                  870                  875                  880

Leu Arg Val Ala Ala Gly Thr Leu Lys Lys Tyr Gly Ala Lys Val Glu
            885                  890                  895

Cys Val Glu Ser Gly Lys Asp Ala Leu Ser Leu Leu Gln Val Pro His
        900                  905                  910

Lys Phe Asp Leu Cys Leu Met Asp Ile Gln Met Pro Glu Met Asp Gly
            915                  920                  925

Phe Glu Ala Thr Arg Gln Ile Arg Ala Met Glu Gly Lys Ala Asn Glu
        930                  935                  940

Gln Ala Asp Asp Ser Glu Ser Gly Ser Glu Ile Ala Ala Lys Thr Ala
945                  950                  955                  960

Lys Trp His Leu Pro Ile Leu Ala Met Thr Ala Asp Val Ile Gln Ala
            965                  970                  975

Thr His Glu Glu Cys Thr Lys Cys Gly Met Asp Gly Tyr Val Ser Lys
        980                  985                  990

Pro Phe Glu Glu Lys Gln Leu Phe Gln Ala Val Gln Lys Phe Leu Gly
        995                  1000                1005

Pro Cys Val Ser Ser
   1010

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
aaggttaggc gtggattcct c                                          21

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
gagatgaagg aatgttcagt cc                                      22

<210> SEQ ID NO 7
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 7
tgggctatta ttgggctttg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
cgtgggataa aaccaccaag                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
caactgccca gctatattgc                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
tttgggacgg aggaagtagt                                              20

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
tgctgccggc gattaacaac t                                            21

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ttcgagacgg ggatttgatg                                              20

<210> SEQ ID NO 13
<211> LENGTH: 19
<212> TYPE: DNA
<213> ORGANISM: Artificial Sequence
<220> FEATURE:
<223> OTHER INFORMATION: Synthetic Construct

<400> SEQUENCE: 13
gatgggttcg catcgtcac                                               19
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
cttacccagt ctcgaggtag                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
gactcagaga cggggactag                                              20

<210> SEQ ID NO 16
<211> LENGTH: 18
<212> TYPE: DNA
<213> ORGANISM: Artificial Sequence
<220> FEATURE:
<223> OTHER INFORMATION: Synthetic Construct

<400> SEQUENCE: 16
cgtggcgact gatcagcg                                                18

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
tggagagagt acagtactac                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
gaagcattgt acttctagtc                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
aggcgcgtag aattcctagt                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 20
aaagctgccc aaactatgcg                                              20

<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
gcttatgcgt cacatcacta c                                            21

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
aaaggtttgc gtacagcgag                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct

<400> SEQUENCE: 23
aagtcaacgg tgtcatacga                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

<400> SEQUENCE: 24
catggtcttg atgatccacc                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
gtgtggctga tgaatcttct                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
ggtgttctga tctcatgaga                                              20

<210> SEQ ID NO 27
```

```
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
cttggagtcg ctacgataat g                                                   21

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct

<400> SEQUENCE: 28
ctggacggta atgggtgcaa                                                     20

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
caagctgaca gctcaacttc                                                     20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
gatagtcaac gaggtggcac                                                     20

<210> SEQ ID NO 31
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31
caaggtaaac ctcagagtgg c                                                   21

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
ccagcaacac acctgtggct                                                     20

<210> SEQ ID NO 33
<211> LENGTH: 20
<212> TYPE: DNA
<213> ORGANISM: Artificial Sequence
<220> FEATURE:
<223> OTHER INFORMATION: Synthetic Construct

<400> SEQUENCE: 33
```

```
ttgttgctct tcaacagagg                                           20

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34
catgttagcc acgatgcctc                                           20

<210> SEQ ID NO 35
<211> LENGTH: 40
<212> TYPE: DNA
<213> ORGANISM: Artificial Sequence
<220> FEATURE:
<223> OTHER INFORMATION: Synthetic Construct

<400> SEQUENCE: 35
ccatgattac gaattccgtg aacaatgtct acgtaggagg                     40

<210> SEQ ID NO 36
<211> LENGTH: 42
<212> TYPE: DNA
<213> ORGANISM: Artificial Sequence
<220> FEATURE:
<223> OTHER INFORMATION: Synthetic Construct

<400> SEQUENCE: 36
gtcaccaatt cacacgtgct accagcctac agcatagtac tc                  42

<210> SEQ ID NO 37
<211> LENGTH: 19
<212> TYPE: DNA
<213> ORGANISM: Artificial Sequence
<220> FEATURE:
<223> OTHER INFORMATION: Synthetic Construct

<400> SEQUENCE: 37
aaccagctga ggcccaaga                                            19

<210> SEQ ID NO 38
<211> LENGTH: 24
<212> TYPE: DNA
<213> ORGANISM: Artificial Sequence
<220> FEATURE:
<223> OTHER INFORMATION: Synthetic Construct

<400> SEQUENCE: 38
acgattgatt taaccagtcc atga                                      24

<210> SEQ ID NO 39
<211> LENGTH: 20
<212> TYPE: DNA
<213> ORGANISM: Artificial Sequence
<220> FEATURE:
<223> OTHER INFORMATION: Synthetic Construct

<400> SEQUENCE: 39
caagattcca atagcccagc                                           20

<210> SEQ ID NO 40
<211> LENGTH: 18
<212> TYPE: DNA
```

```
<213> ORGANISM: Artificial Sequence
<220> FEATURE:
<223> OTHER INFORMATION: Synthetic Construct

<400> SEQUENCE: 40
gcctgtcgct tcatcgtc                                               18
```